United States Patent [19]

Bailey

[11] Patent Number: 4,539,429

[45] Date of Patent: Sep. 3, 1985

[54] SUBSTITUTED AMINOPHENYLALKYL KETONES, THEIR PREPARATION AND USE

[75] Inventor: Denis M. Bailey, East Greenbush, N.Y.

[73] Assignee: Sterling Drug Inc., New York, N.Y.

[21] Appl. No.: 512,791

[22] Filed: Jul. 11, 1983

[51] Int. Cl.$^3$ .............................................. C07C 87/50
[52] U.S. Cl. ..................... 514/658; 564/433
[58] Field of Search ........................ 564/433; 424/330

[56] References Cited

U.S. PATENT DOCUMENTS 2,075,359 3/1937 Salzberg et al. .................... 424/250
3,432,507 3/1969 Paquette ................. 546/81

OTHER PUBLICATIONS

Wagner & Zook; Synthetic Organic Chemistry (Wiley & Sons 1953) pp. 171-172.
CA: 67, 81925p, (1967), J. R. Geigy A.G.

*Primary Examiner*—Charles F. Warren
*Assistant Examiner*—Harry B. Shubin
*Attorney, Agent, or Firm*—Thomas L. Johnson; B. Woodrow Wyatt; Paul E. Dupont

[57] ABSTRACT

Novel lower-alkyl 2-(hydroxyphenylamino)phenyl ketones, useful as inhibitors of lipoxygenase activity, are of the formula

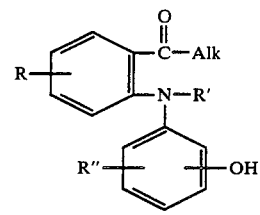

wherein R is hydrogen, lower-alkyl, lower-alkoxy or halo; R' is hydrogen or lower-alkyl; R" is hydrogen, lower-alkyl or halo; and Alk is lower-alkyl. The compounds are prepared by de-etherification of the corresponding alkyl or benzyl ethers which are in turn prepared by reacting a 2-(alkoxy- or benzyloxyphenylamino)benzoic acid with an alkyllithium.

7 Claims, No Drawings

SUBSTITUTED AMINOPHENYLALKYL KETONES, THEIR PREPARATION AND USE

BACKGROUND OF THE INVENTION (1) Field of the Invention

The present invention relates to novel lower-alkyl 2-(hydroxyphenylamino)phenyl ketones, a process for the preparation thereof, and the use of said esters as agents which inhibit lipoxygenase activity.

(2) Information Disclosure Statement

Bell et al., J. Med. Chem. 13, 664 (1970) disclose 2-(4-methoxyphenylamino)phenyl methyl ketone (compound 16). No utility is disclosed for the compound.

Montanari, Boll. Sci. fac. chim. Bologna 17, 33–43 (1959);(Chemical Abstracts 54:3291i) disclose 4-(4-hydroxyphenylamino)methyl ketone, prepared for spectral studies only.

The subject matter of this application is in part disclosed but not claimed in copending Schlegel and Bell U.S. patent application, Ser. No. 485,936, filed Apr. 18, 1983, now U.S. Pat. No. 4,496,590, issued Jan. 29, 1985.

SUMMARY OF THE INVENTION

In a product aspect, the invention relates to compounds of the formula

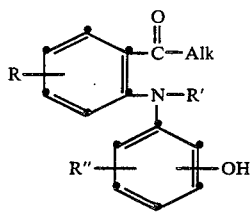

I wherein:
R is hydrogen, lower-alkyl, lower-alkoxy or halo;
R' is hydrogen or lower-alkyl;
R" is hydrogen, lower-alkyl or halo; and
Alk is lower-alkyl.

In a process aspect, the invention relates to a process for preparing a compound of Formula I which comprises de-etherifying a compound of the formula

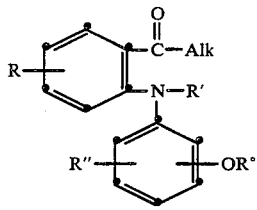

II wherein R° is benzyl or lower-alkyl by a method selected from:

(a) catalytically hydrogenating a compound where R° is benzyl; and
(b) treating a compound where R° is benzyl or lower-alkyl and R is other than lower-alkoxy with a strong protonic acid or a Lewis acid.

In a further product aspect, the invention relates to compositions for inhibiting lipoxygenase activity which comprises a compound of Formula I together with one or more pharmaceutically acceptable excipients or diluents.

In a further process aspect, the invention relates to a method for inhibiting lipoxygenase activity in a mammal which comprises administering to said mammal a pharmacologically effective amount of a composition comprising a compound of Formula I together with one or more pharmaceutically acceptable excipients or diluents.

DETAILED DESCRIPTION INCLUSIVE OF PREFERRED EMBODIMENTS

In the foregoing Formulas I and II, the variables R, R', R", R° and Alk when they stand for lower-alkyl or lower-alkoxy include such groups containing from one to three carbon atoms; and when R or R" stands for halo, it can be any of the common halogens, fluorine, chlorine, bromine or iodine.

The synthetic approach to the compounds of the invention is outlined in the following flow sheet:

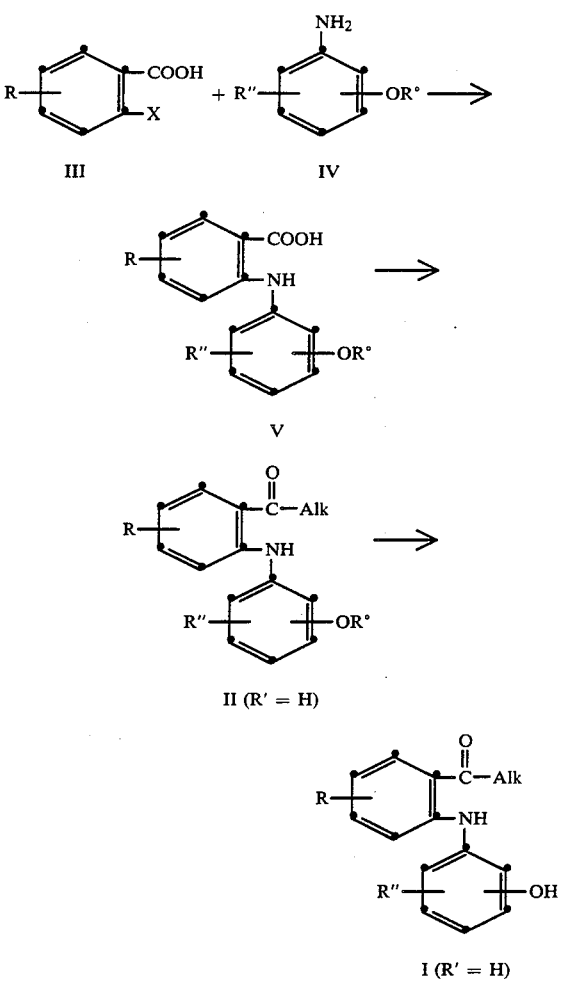

A 2-halobenzoic acid (III, where X is Cl, Br or I) is caused to react with an aminophenol ether (IV), usually in the presence of a catalyst such as cupric acetate, to yield an anthanilic acid derivative of Formula V. In these formulas, R, R" and R° have the meanings given hereinabove.

An acid of Formula V reacts with a lower-alkyllithium to cause replacement of the carboxyl group by a lower-alkanoyl group, thereby forming a ketone of Formula II (R'=H). The final step is a de-etherification in which a compound of Formula II (R′=H) is converted to a phenolic ketone of Formula I (R′=H) by dealkylation (R°=lower-alkyl) with a protonic or Lewis acid, or debenzylation (R°=benzyl) by catalytic hydrogenation or acid treatment. A preferred reagent for dealkylation is boron tribromide.

If a compound of Formula I where R′ is lower-alkyl is desired, it can be obtained by N-alkylation of an intermediate of Formula II (R′=H), followed by de-etherification. The N-alkylation is effected with a lower-alkyl halide (preferably bromide or iodide) in the presence of a strong base.

The following examples will illustrate the invention.

EXAMPLE 1

(a) 2-(4-Benzyloxyphenylamino)-5-methoxybenzoic acid

[V; R=5-CH$_3$O, OR°=4-OCH$_2$C$_6$H$_5$, R″=H]

A mixture of 231 g of 2-bromo-5-methoxybenzoic acid, 262 g of 4-benzyloxyaniline hydrochloride, 160 g of potassium carbonate and 2 g of activated copper powder in about 2100 ml of amyl alcohol was heated at reflux with stirring for 4.5 hours. The reaction mixture was concentrated in vacuo and the residue dissolved in 6 liters of water. The solution was filtered and acidified with hydrochloric acid. The solid which formed was collected and recrystallized twice from benzene-cyclohexane to give 245 g of 2-(4-benzyloxyphenylamino)-5-methoxybenzoic acid, m.p. 167°–168° C.

(b) 1-[2-(4-Benzyloxyphenylamino)-5-methoxyphenyl]ethanone

[II; R=5-CH$_3$O, R′ and R″=H, OR°=4-OCH$_2$C$_6$H$_5$, Alk=CH$_3$]

Methyllithium (210 ml, 1.25M methyllithium-lithium bromide complex in ether) (0.263 mole) was added dropwise to a solution of 25.49 g (0.0732 mole) of 2-(4-benzyloxyphenylamino)-5-methoxybenzoic acid in 226 ml of tetrahydrofuran cooled to 0°–5° C. The reaction mixture was stirred for 3 hours at 0°–5° C. Ethyl acetate was then added and the mixture poured into ice and saturated ammonium chloride solution. The aqueous suspension was extracted with ether, the ether extracts dried over anhydrous magnesium sulfate and concentrated. The residue was recrystallized from toluene to give 16.1 g of 1-[2-(4-benzyloxyphenylamino)-5-methoxyphenyl]ethanone, yellow-orange solid, m.p. 80°–81.5° C.

(c) 1-[2-(4-Hydroxyphenylamino)-5-methoxyphenyl]ethanone

[I; R=5-CH$_3$O, R′ and R″=H, OH at 4-position, Alk=CH$_3$]

1-[2-(4-Benzyloxyphenylamino)-5-methoxyphenyl]ethanone (9 g, 0.0258 mole) in 810 ml of ethanol and 90 ml of acetic acid was hydrogenated in a Parr apparatus in the presence of 900 mg of 10% palladium-on-carbon catalyst. After the required amount of hydrogen had been consumed, the reaction mixture was filtered and the solvents removed in vacuo. The residue was partitioned between ether and 10% aqueous sodium bicarbonate. The ether extracts were dried (MgSO$_4$), the solvent removed, and the residue chromatographed on silica gel using chloroform as the eluant. There was obtained 5.33 g of 1-[2-(4-hydroxyphenylamino)-5-methoxyphenyl]ethanone, orange solid, m.p. 118°–119° C.

If the foregoing procedures are carried out except that the methyllithium in reaction (b) is replaced by ethyllithium, propyllithium or isopropyllithium, each as the lithium bromide complex, it is contemplated that there will be obtained, respectively, 1-[2-(4-hydroxyphenylamino)-5-methoxyphenyl]-1-propanone [I; R=5-CH$_3$O, R′ and R″=H, OH at 4-position, Alk=CH$_2$CH$_3$]; 1-[2-(4-hydroxyphenylamino)-5-methoxyphenyl]-1-butanone [I; R=5-CH$_3$O, R′ and R″=H, OH at 4-position, Alk=CH$_2$CH$_2$CH$_3$]; or 1-[2-(4-hydroxyphenylamino)-5-methoxyphenyl]-2-methyl-1-propanone [I; R=5-CH$_3$O, R′ and R″=H, OH at 4-position, Alk=CH(CH$_3$)$_2$].

EXAMPLE 2

(a) 2-(4-Benzyloxyphenylamino)benzoic acid

[V; R and R″=H, OR°=4-OCH$_2$C$_6$H$_5$] was prepared from 2-chlorobenzoic acid and 4-benzyloxyaniline hydrochloride according to the procedure of Example 1, part (a), and the crude product was used directly in the following reaction.

(b) 1-[2-(4-Benzyloxyphenylamino)phenyl]ethanone

[II; R, R′ and R″=H, OR°=4-OCH$_2$C$_6$H$_5$, Alk=CH$_3$]

Methyllithium as the lithium bromide complex (280 ml, 1M in ether) (0.35 mole) was added slowly to a solution of 31.9 g (0.1 mole) of 2-(4-benzyloxyphenylamino)benzoic acid in 300 ml of tetrahydrofuran cooled to 0°–5° C. The reaction mixture was stirred at 0°–5° C. for 75 minutes and worked up by the procedure described in Example 1, part (b). The product was recrystallized from isopropyl alcohol to give 24 g of 1-[2-(4-benzyloxyphenylamino)phenyl]ethanone.

(c) 1-[2-(4-Hydroxyphenylamino)phenyl]ethanone

[I; R, R′ and R″=H, OH at 4-position, Alk=CH$_3$]

1-[2-(4-Benzyloxyphenylamino)phenyl]ethanone (9 g) in 900 ml of ethanol and 90 ml of acetic acid was hydrogenated in the presence of 1 g of 10% palladium-on-carbon catalyst. The product was isolated and recrystallized from acetonitrile to yield 3.6 g of 1-[2-(4-hydroxyphenylamino)phenyl]ethanone, orange solid, m.p. 168°–169° C.

EXAMPLE 3

(a) 5-Chloro-2-(4-benzyloxyphenylamino)benzoic acid

[V; R=5-Cl, OR°=4-OCH$_2$C$_6$H$_5$, R″=H] was prepared from 2,5-dichlorobenzoic acid and 4-benzyloxyaniline according to the procedure of Example 1, part (a) and was obtained as a yellowish-green solid, m.p. 189°–191° C.

(b) 1-[2-(4-Benzyloxyphenylamino)-5-chlorophenyl]ethanone

[II; R=5-Cl, R′ and R″=H, OR°=4-OCH$_2$C$_6$H$_5$, Alk=CH$_3$] was prepared from 5-chloro-2-(4-benzyloxyphenylamino)benzoic acid and methyllithium according to the procedure of Example 1, part (a), and obtained in about 80% yield as a yellow solid, m.p. 74°–75° C. when recrystallized from cyclohexane.

(c)
1-[5-Chloro-2-(4-hydroxyphenylamino)phenyl]ethanone

[I; R=5-Cl, R' and R''=H, OH at 4-position, Alk=CH₃] was prepared by hydrogenation of 1-[2-(4-benzyloxyphenylamino)-5-chlorophenyl]ethanone according to the procedure of Example 1,part (c). In this case the product was obtained as a mixture with the corresponding compound when the 5-chloro atom was replaced by hydrogen. The mixture was separated by high pressure liquid chromatography using ethyl acetate-hexane as eluant, to afford 1-[5-chloro-2-(4-hydroxyphenylamino)phenyl]ethanone as a yellow solid, m.p. 158°–161° C.

EXAMPLE 4

(a) 2-(2-Methoxyphenylamino)benzoic acid

[V; R and R''=H, OR°=2-OCH₃]

A mixture of 40 g (0.25 mole) of 2-chlorobenzoic acid, 21 ml (0.26 mole) of 2-methoxyaniline, 3.84 g cupric acetate, 35.4 g of potassium carbonate and 155 ml of dimethylformamide was heated at 120° C. for 12 hours. The reaction mixture was poured into ice-water, neutralized with concentrated hydrochloric acid to pH 2, and stirred for one hour. The solid product was collected by filtration, air dried and recrystallized from toluene to give 28.61 g of 2-(2-methoxyphenylamino)benzoic acid.

(b) 1-[2-(2-Methoxyphenylamino)phenyl]ethanone

[II; R, R' and R''=H, OR°=2-OCH₃, Alk=CH₃] is obtainable by reacting 2-(2-methoxyphenylamino)benzoic acid with methyllithium by the procedure of Example 1(b).

(c) 1-[2-(2-Hydroxyphenylamino)phenyl]ethanone

[I; R, R' and R''=H, OH at 2-position, Alk=CH₃] is obtainable by reacting 1-[2-(2-methoxyphenylamino)phenyl]ethanone with boron tribromide. A preferred procedure comprises adding boron tribromide in an inert solvent such as methylene dichloride dropwise to a solution of the methoxy compound in an inert solvent, e.g. methylene dichloride cooled to a low temperature (−40° to −80° C.) and then stirring the mixture for several hours.

EXAMPLE 5

(a) 2-(4-Methoxy-2-methylphenylamino)benzoic acid

[V; R=H, R''=2-CH₃, OR°=4-OCH₃] was prepared from 2-chlorobenzoic acid and 4-methoxy-2-methylaniline according to the procedure of Example 1, part (a), and was obtained in 59% yield as a grey solid.

(b) 1-[2-(4-Methoxy-2-methylphenylamino)phenyl]ethanone

[II; R and R'=H, R''=2-CH₃, OR°=4-OCH₃, Alk=CH₃] is obtainable by reacting 2-(4-methoxy-2-methylphenylamino)benzoic acid with methyllithium by the procedure of Example 1(b).

(c) 1-[2-(4-Hydroxy-2-methylphenylamino)phenyl]ethanone

[I; R and R'=H, R''=2-CH₃, OH at 4-position, Alk=CH₃] is obtainable by reacting 1-[2-(4-methoxy-2-methylphenylamino)phenyl]ethanone with boron tribromide.

EXAMPLE 6

(a) 2-(3-Chloro-4-methoxyphenylamino)benzoic acid

[V; R=H, R''=3-Cl, OR°=4-OCH₃] was prepared from 2-chlorobenzoic acid and 3-chloro-4-methoxyaniline according to the procedure of Example 1, part (a), and was obtained in 68% yield as a solid recrystallized from acetonitrile.

(b) 1-[2-(3-Chloro-4-methoxyphenylamino)phenyl]ethanone

[II; R and R'=H, R''=3-Cl, OR°=4-OCH₃, Alk=CH₃] is obtainable by reacting 2-(3-chloro-4-methoxyphenylamino)benzoic acid with methyllithium by the procedure of Example 1(b).

(c) 1-[2-(3-Chloro-4-hydroxyphenylamino)phenyl]ethanone

[I; R and R'=H, R''=3-Cl, OH at 4-position, Alk=CH₃] is obtainable by reacting 1-[2-(3-chloro-4-methoxyphenylamino)phenyl]ethanone with boron tribromide.

EXAMPLE 7

(a) 4-Chloro-2-(4-methoxyphenylamino)benzoic acid

[V; R=4-Cl, R''=H, OR°=4-OCH₃] was prepared from 2,4-dichlorobenzoic acid and 4-methoxyaniline according to the procedure of Example 1, part (a), and was obtained in about 60% yield as a green-grey solid.

(b) 1-[2-(4-Methoxyphenylamino)-4-chlorophenyl]ethanone

[II; R=4-Cl, R' and R''=H, OR°=4-OCH₃, Alk=CH₃] is obtainable by reacting 4-chloro-2-(4-methoxyphenylamino)benzoic acid with methyllithium by the procedure of Example 1(b).

(c) 1-[2-(4-Hydroxyphenylamino)-4-chlorophenyl]ethanone

[I; R=4-Cl, R' and R''=H, OH at 4-position, Alk=CH₃] is obtainable by reacting 1-[2-(4-methoxyphenylamino)-4-chlorophenyl]ethanone with boron tribromide.

EXAMPLE 8

(a) 1-{2-[4-Benzyloxyphenyl(N-methyl)amino]-5-methoxyphenyl}ethanone

[II; R=5-CH₃O, R'=CH₃, R''=H, OR°=4-OCH₂C₆H₅, Alk=CH₃] is obtainable by N-alkylation of 1-[2-(4-benzyloxyphenylamino)-5-methoxyphenyl]ethanone (Example 1b) with methyl iodide in the presence of sodium hydride. A preferred procedure is to add slowly methyl iodide in excess to a cooled (0° C.) suspension of starting material and sodium hydride in an inert solvent, e.g. dimethylformamide, and stirring the reaction mixture at ambient temperature until the reaction is complete.

(b)

1-{2-[4-Hydroxyphenyl(N-methyl)amino]-5-methoxyphenyl}ethanone

[I; R=5-CH$_3$O, R'=CH$_3$, R''=H, OH at 4-position, Alk=CH$_3$] is obtainable by catalytic hydrogenation of 1-{2-[4-benzyloxyphenyl(N-methyl)amino]-5-methoxyphenyl}ethanone according to the procedure of Example 1, part (c).

The compounds of Formula I have been found to inhibit lipoxygenase activity in biological systems, thus indicating their usefulness as anti-asthmatic agents.

Slow reacting substance of anaphylaxis (SRS-A) is a descriptive term for a family of lipoxygenase metabolic products of arachidonic acid designated as the leukotrienes. These substances are potent contractile agents of vascular and pulmonary smooth muscle. The relationship of SRS-A to asthma was first characterized by Brockelhurst [Rev. in Adv. Drug Res. 19, 109 (1970)] who identified the material as being present subsequent to specific antigen challenge of living tissue obtained from asthmatic patients. Herxheimer and Stressmann [J. Physiol. 165, 78P (1953)] first demonstrated that aerosolized guinea pig SRS-A induced bronchospasm in man. This observation has been more recently confirmed using purified leukotrienes.

Recent studies have indicated that lipoxygenase inhibiting compounds may have therapeutic potential in treating diseased states other than asthma, e.g. bronchitis, acute inflammation, arthritis, psoriasis, cardiovascular insufficiency and myocardial infarct.

The primary screening test used is a determination of the inhibition of lipoxygenase and cyclooxygenase derived from rat basophilic leukemia (RBL-1) cells. The test was carried out according to the following procedure:

Single cell suspensions of RBL-1 cells are homogenized to obtain the microsomal fraction containing lipoxygenase and cyclooxygenase. Test compounds are added to the enzyme-containing homogenate for a 5 min preincubation period at 37° C. prior to the additon of $^{14}$C-arachidonic acid substrate. Following incubation at 37° C. for 15 min, the reaction is stopped by the addition of 2M formic acid and the enzyme-substrate products are extracted into chloroform. An aliquot of the extract is evaporated to dryness, reconstituted in ether to 1/10 original volume, spotted on thin layer chromatography plates and chromatographed. The peak areas of radioactivity representing the products are located by scanning the plates. The quantity of products formed is estimated by measuring the height of the radioactivity peaks observed on the chromatographic scans. Alternatively, the areas of radioactivity are scraped from the plate and the $^{14}$C quantitated by scintillation counting. The percent inhibition in the formation of the cyclooxygenase product PGD2, designated as Cl and lipoxygenase products, L1 designated for 5,12-di-HETE and L2 for 5-HETE are shown. Compounds with >50% inhibition of L1 and L2 at a screening concentration of 1 μM are considered active.

The in vivo activity was measured by the effect on the SRS-A component of immunologically induced bronchoconstriction in guinea pigs. The test was carried out according to the following procedure:

Two weeks after immunization with egg albumin, guinea pigs are prepared for bronchoconstriction determination. One hour prior to antigen challenge, each animal is dosed orally with indomethacin and chlorpheniramine. Animals are anesthetized with sodium pentobarbital, the trachea cannulated and the animal artificially respired. Arachidonic acid is administered intravenously prior to antigen challenge. The resulting bronchoconstriction is recorded by the standard lung overflow procedure and the peak increase in intratracheal pressure (mm Hg) over a 10 minute observation period is recorded. Compounds are evaluated for their ability to prevent the increased intratracheal pressure in an experimental group of animals as compared to the medicated (indomethacin+chlorpheniramine+arachidonic acid) control group. The results are expressed in terms of percent inhibition or as ED$_{50}$ values (effective dose in 50% of the animals).

The following Table summarizes the results obtained from the testing of specific compounds of the invention.

| Example No. | In vitro | | IC$_{50}$[b] | In vivo Guinea Pig |
|---|---|---|---|---|
| | % Inhibition[a] | | | |
| 1c | Cl | 36 | >1 | ED$_{50}$ = 2.7 mg/kg i.v. |
| | L1 | 88 | 0.07 | 52% inhib. |
| | L2 | 88 | 0.07 | at 1 mg/kg orally |
| 2c | Cl | 9 | | |
| | L1 | 61 | | |
| | L2 | 72 | | |

[a]Percent inhibition of cyclooxygenase (Cl) and lipoxygenase (L1 and L2) formation at a dose of 1 μM.
[b]Inhibitory concentration (μM) in 50% of tests.

The compounds of the invention can be prepared for use by conventional pharmaceutical procedures: that is, by dissolving or suspending them in a pharmaceutically acceptable vehicle, e.g., water, aqueous alcohol, glycol, oil solution or oil-water emulsion, for parenteral or oral administration; or by incorporating them in unit dosage form as capsules or tablets for oral administration either alone or in combination with conventional adjuvants or excipients, e.g., calcium carbonate, starch, lactose, talc, magnesium stearate, gum acacia, and the like.

I claim:
1. A compound of the formula

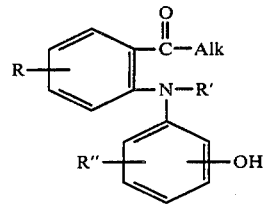

wherein:
R is hydrogen, lower-alkyl, lower-alkoxy or halo;
R' is hydrogen or lower-alkyl;
R'' is hydrogen, lower-alkyl or halo; and
Alk is lower-alkyl.
2. A compound according to claim 1 wherein R' is hydrogen and Alk is methyl.
3. 1-[2-(4-Hydroxyphenylamino)phenyl]ethanone, according to claim 2.
4. 1-[2-(4-Hydroxyphenylamino)-5-methoxyphenyl]ethanone, according to claim 2.
5. A composition for inhibiting lipoxygenase activity which comprises a compound according to claim 1 together with one or more pharamceutically acceptable excipients or diluents.

6. A method for inhibiting lipoxygenase activity in a mammal which comprises administering to said mammal a pharmacologically effective amount of a composition according to claim 5.

7. A method of treating or preventing allergic asthma in a mammal which comprises administering to said mammal an anti-asthmatically effective amount of a composition according to claim 5.

* * * * *